US008632546B2

(12) United States Patent
Sackett et al.

(10) Patent No.: US 8,632,546 B2
(45) Date of Patent: Jan. 21, 2014

(54) EXPANDABLE PROXIMAL REAMER

(75) Inventors: Samuel G. Sackett, Fort Wayne, IN (US); Jonathan E Carr, Warsaw, IN (US); Larry G McCleary, Warsaw, IN (US)

(73) Assignee: Depuy Synthes Products, LLC, Raynham, MA (US)

( * ) Notice: Subject to any disclaimer, the term of this patent is extended or adjusted under 35 U.S.C. 154(b) by 303 days.

(21) Appl. No.: 13/069,470

(22) Filed: Mar. 23, 2011

(65) Prior Publication Data

US 2011/0172670 A1 Jul. 14, 2011

Related U.S. Application Data

(60) Division of application No. 11/858,939, filed on Sep. 21, 2007, now Pat. No. 7,935,117, and a continuation-in-part of application No. 11/743,325, filed on May 2, 2007, now abandoned.

(51) Int. Cl.
*A61B 17/00* (2006.01)
*A61B 17/58* (2006.01)
*A61B 17/56* (2006.01)
*A61F 2/30* (2006.01)

(52) U.S. Cl.
USPC ............................... 606/80; 606/63; 606/68

(58) Field of Classification Search
USPC .............................................. 606/80, 63, 68
See application file for complete search history.

(56) References Cited

U.S. PATENT DOCUMENTS

| 2,091,628 | A | 8/1937 | Carlson |
| 3,702,611 | A | 11/1972 | Fishbein |
| 4,047,829 | A | 9/1977 | Benjamin et al. |
| 4,050,840 | A | 9/1977 | Skingle |
| 5,122,134 | A | 6/1992 | Borzone et al. |
| 5,190,548 | A | 3/1993 | Davis |
| 5,904,686 | A | 5/1999 | Zucherman et al. |
| 6,117,138 | A | 9/2000 | Burrows et al. |
| 6,224,604 | B1 | 5/2001 | Suddaby |
| 6,238,398 | B1 | 5/2001 | Lechot |
| 6,383,188 | B2 | 5/2002 | Kuslich et al. |
| 6,517,581 | B2 | 2/2003 | Blamey |
| 6,818,914 | B2 | 11/2004 | Ishii et al. |
| 6,840,944 | B2 | 1/2005 | Suddaby |
| 6,902,568 | B2 | 6/2005 | Serhan |

(Continued)

FOREIGN PATENT DOCUMENTS

| EP | 1346694 A | 9/2003 |
| JP | 05323787 | 11/2005 |
| WO | WO 00/12832 A | 3/2000 |

OTHER PUBLICATIONS

European Search Report for Corresponding EPO Application No. 08251572.7-1526 Dated Dec. 1, 2008, 10 pages.

(Continued)

*Primary Examiner* — Sameh Boles

(57) ABSTRACT

A reamer for reaming a portion of a long bone cavity for use in implanting a joint prosthesis. The reamer is used in cooperation with a portion of an orthopaedic implant component and includes an expandable body that is adapted to adjust between a plurality of diameters. A plurality of cutting edges are also included and extend outwardly from the body, the edges adapted for cooperation with bone, and the cutting edges expanding as the expandable body expands.

4 Claims, 15 Drawing Sheets

(56) References Cited

U.S. PATENT DOCUMENTS

| | | |
|---|---|---|
| 7,229,457 B2 | 6/2007 | Murphy et al. |
| 7,632,276 B2 | 12/2009 | Fishbein |
| 7,674,265 B2 | 3/2010 | Smith et al. |
| 2002/0095214 A1 | 7/2002 | Hyde |
| 2005/0075638 A1 | 4/2005 | Collazo |
| 2005/0096685 A1* | 5/2005 | Murphy et al. ............... 606/180 |
| 2005/0113836 A1 | 5/2005 | Lozier et al. |
| 2006/0217730 A1 | 9/2006 | Termanini |

OTHER PUBLICATIONS

European Search Report for Corresponding EPO Application No. 10189191.9-1526 Dated Jan. 14, 2011, 10 Pages.

Japanese Search Report From Corresponding Japanese Patent Application No. JP2008-119562, Dated Dec. 4, 2012, 3 Pages.

* cited by examiner

EXPANDABLE PROXIMAL REAMER

RELATED APPLICATIONS

This application is a divisional patent application of U.S. patent application Ser. No. 11/858,939 of the same title and filed on Sep. 21, 2007, which was a continuation-in-part of U.S. Ser. No. 11/743,325, filed on May 2, 2007, both herein incorporated by reference in their entireties.

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

Currently in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck offsets, head offsets and leg lengths. The combination of these four factors affects the laxity of the soft tissue. By optimizing the biomechanics, the surgeon can provide a patient a stable hip that is more resistant to dislocation.

In order to accommodate the range of patient arthropathy metrics, a wide range of hip implant geometries are currently manufactured by DePuy Orthopaedics, Inc., the assignee of the current application, and by other companies. In particular, the S-ROM® total hip systems offered by DePuy Orthopaedics, Inc. may include up to six neck offsets per stem diameter, six head lengths and one leg length adjustment. The combination of all these biomechanic options is rather complex.

Anteversion of a total hip system is closely linked to the stability of the joint. Improper anteversion can lead to dislocation and patient dissatisfaction. Anteversion control is important in all hip stems. However, it is a more challenging issue with the advent of stems with additional modularity.

The prior art has provided for some addressing of the anteversion problem. For example, the current S-ROM® stems have laser markings on the medial stem and the proximal sleeve. This marking enables the surgeon to measure relative alignment between these components. Since the sleeve has infinite anteversion, it is not necessarily oriented relative to a bony landmark that can be used to define anteversion. In fact, the current sleeves are sometimes oriented with the spout pointing directly laterally into the remaining available bone.

When a primary or index total joint arthroplasty fails, a revision procedure is performed in which the index devices (some or all) are removed. Quite often the remaining bone is significantly compromised compared to a primary hip procedure. Significant bone loss is observed, often with a lack of bone landmarks typically used for alignment.

In a common step in the surgical procedure known as total hip arthroplasty, a trial or substitute stem is first implanted into the patient. The trial is utilized to verify the selected size and shape of the implant in situ on the patient and the patient is subjected to what is known as a trial reduction. This trial reduction represents moving the joint, including the trial implant through selected typical motions for that joint. Current hip instruments provide a series of trials of different sizes to help the surgeon assess the fit and position of the implant. Trials, which are also known as provisionals, allow the surgeon to perform a trial reduction to assess the suitability of the implant and the implant's stability prior to final implant selection. In order to reduce inventory costs and complexity, many trialing systems are modular. For example, in the Excel™ Instrument System, a product of DePuy Orthopaedics, Inc., there is a series of broaches and a series of neck trials that can be mixed and matched to represent the full range of implants. There is a single fixed relationship between a broach and a neck trial, because these trials represent a system of monolithic stem implants.

Likewise, in the current S-ROM® instrument systems provided by DePuy Orthopaedics, Inc., there are neck trials, proximal body trials, distal stem trials, head trials and sleeve trials. By combining all of these components, the implant is represented. Since the S-ROM® stem is modular and includes a stem and a sleeve, the angular relationship or relative anteversion between the neck and the sleeve is independent and represented by teeth mating between the neck and the proximal body trial. The proximal body trial has fixed transverse bolts that are keyed to the sleeve in the trialing for straight, primary stems. The long stem trials do not have the transverse bolts and are thus not rotationally stable during trial reduction and therefore are not always used by the surgeon.

With the introduction of additional implant modularity, the need for independent positioning of the distal stem, proximal body and any sleeve that comprise the implants is required. Currently, modular stems for one replacement may come with up to thirty four different sleeve geometries, requiring up to seven different reamer attachments and corresponding pilot shafts to prepare the cone region of the sleeve.

While the prior art has attempted to reduce the steps in surgical techniques and improve the ability to precisely remove bone to prepare the bone for receiving a proximal component, the need remains for a system and apparatus to reduce the number of components required to perform hip arthroplasty.

The present invention is directed to alleviate at least some of the problems with the prior art.

SUMMARY OF THE INVENTION

According to one embodiment of the present invention, a reamer for reaming a portion of a long bone cavity for use in implanting a joint prosthesis is provided. The reamer is for cooperation with a portion of an orthopaedic implant component and includes an expandable body that is adapted to adjust between a plurality of diameters. A plurality of cutting edges extending outwardly from the body is also included. The edges are adapted for cooperation with bone, such that the cutting edges expand as the expandable body expands.

According to another embodiment of the present invention, a method for reaming a portion of a long bone cavity for use in implanting a joint prosthesis is provided. The reamer is used in cooperation with a portion of an orthopaedic implant component. The method includes reaming a distal portion of the long bone using a distal reamer as well as reaming a proximal portion of the long bone using a proximal reamer. At least one of the distal reamer and proximal reamer is an expandable reamer, such that one of the distal reamer and proximal reamer includes an expandable body adapted to adjust between a plurality of diameters.

According to yet another embodiment of the present invention, a kit for reaming a portion of a long bone cavity for use in implanting a joint prosthesis is provided. The reamers are used in cooperation with portions of an orthopaedic implant component. The kit includes a distal reamer for reaming a distal portion of the long bone, a proximal reamer for reaming a proximal portion of the long bone, and a pilot shaft for insertion into a reamed distal portion and attachment to the proximal reamer during the reaming of the proximal portion. At least one of the distal reamer, proximal reamer, and pilot shaft is expandable, such that one of the distal reamer, proximal reamer, and pilot shaft includes an expandable body adapted to adjust between a plurality of diameters.

According to another embodiment of the present invention, a reamer for reaming a portion of a long bone cavity for use in implanting a joint prosthesis is provided. The reamer is for cooperation with a portion of an orthopaedic implant component and includes a body. The body includes a hollow housing having a plurality of slots adapted to adjust between a plurality of diameters. A plurality of cutting edges extend through the plurality of slots and the edges are adapted for cooperation with bone. Each of the plurality of cutting edges includes a plurality of ridges. An actuator rod is included and has a gear that engages the plurality of ridges, such that when the actuator rod is turned in one direction, the plurality of cutting edges expands through the plurality of slots to alter the cutting diameter of the reamer.

According to yet another embodiment of the present invention, a method for reaming a portion of a long bone cavity for use in implanting a joint prosthesis is provided. The reamer cooperates with a portion of an orthopaedic implant component. The method includes reaming a cylindrical portion of the long bone using a cylindrical reamer and reaming a conical portion of the long bone using a conical reamer. At least one of the cylindrical reamer and conical reamer is an expandable reamer, such that at least one of the cylindrical reamer and conical reamer includes a body having a plurality of slots. The expandable reamer also includes a plurality of cutting edges extending through the slots and an actuator rod including a gear for engaging the plurality of cutting edges such that when the actuator rod is turned in one direction, the plurality of cutting edges expands outwardly through the slots to alter the cutting diameter of the reamer.

According to another embodiment of the present invention, a kit for reaming a portion of a long bone cavity for use in implanting a joint prosthesis is provided. The reamers cooperate with portions of an orthopaedic implant component. The kit comprises a distal reamer for reaming a distal portion of the long bone, a proximal reamer for reaming a proximal portion of the long bone, and a pilot shaft for insertion into a reamed distal portion and attachment to the proximal reamer during the reaming of the proximal portion. At least one of the distal reamer, proximal reamer, and pilot shaft is expandable, such that at least one of the distal reamer, proximal reamer, and pilot shaft includes a body having a plurality of slots, a plurality of cutting edges extending through the slots, and an actuator rod including a gear for engaging the plurality of cutting edges such that when the actuator rod is turned in one direction, the plurality of cutting edges expands outwardly through the slots to alter the cutting diameter of the reamer.

BRIEF DESCRIPTION OF THE DRAWINGS

For a more complete understanding of the present invention and the advantages thereof, reference is now made to the following description taken in connection with the accompanying drawings, in which.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
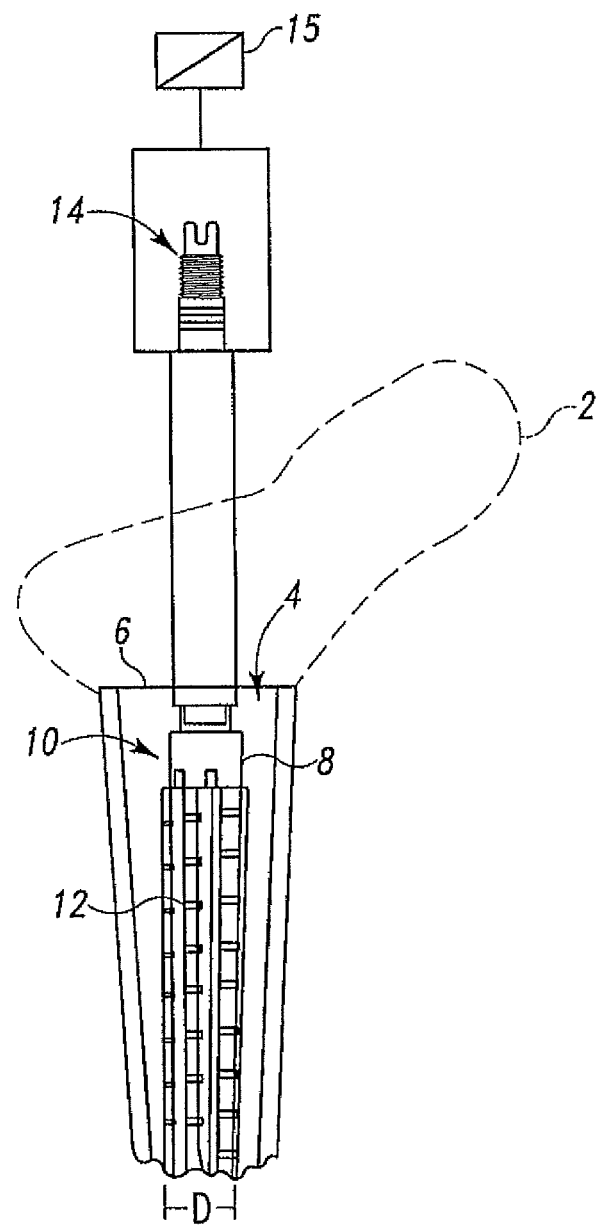
FIG. 1 is a plan view of a distal reamer in position in a long bone for preparing a bone canal for receiving a long bone prosthetic stem.

Referring now to FIG. 1 a long bone or femur 2 for use with the present invention is shown. The femur 2 includes an intermedullary canal 4 into which the prosthesis of the present invention may be inserted. The femur 2 is resected along resection line 6 by, for example, a power tool, for example, a saw. The resecting of the long bone or femur 2 exposes the intermedullary canal 4 of femur 2. A distal or cylindrical reamer 8 that may be a standard commercially available reamer is positioned in the intermedullary canal 4 of the long bone 2 to form cavity 10 for receiving an orthopedic joint implant. The distal reamer 8 includes a plurality of longitudinally extending channels, or flutes 12 which are used to remove bone and other biological matter from the intermedullary canal 4 to form the cavity 10. The distal reamer 8 may be rotated by use of a connector 14 positioned on the distal reamer 8. The connector 14 may be any standard connector for example a Hudson or an A-O connector. The connector 14 is used to connect to a power tool 15 for rotating the distal reamer 8. The power tool 15 may be any standard power tool. It should be appreciated that the distal reamer 8 may be rotated through the use of the connector 14 by a hand tool for example a "T" shaped handle.

The diameter "D" of the distal reamer 8 is determined by the size of the distal stem (not shown) that is to be implanted into the femur 2. Because of variances in human anatomy, there are numerous sizes of distal stems that can be implanted. Therefore, there are numerous sizes of reamers 8 that can also be used. The large number of reamers 8 can increase production and manufacturing costs, as well as create problems during the surgery should the doctor select the wrong size distal reamer 8 to be used.

Figure 2:
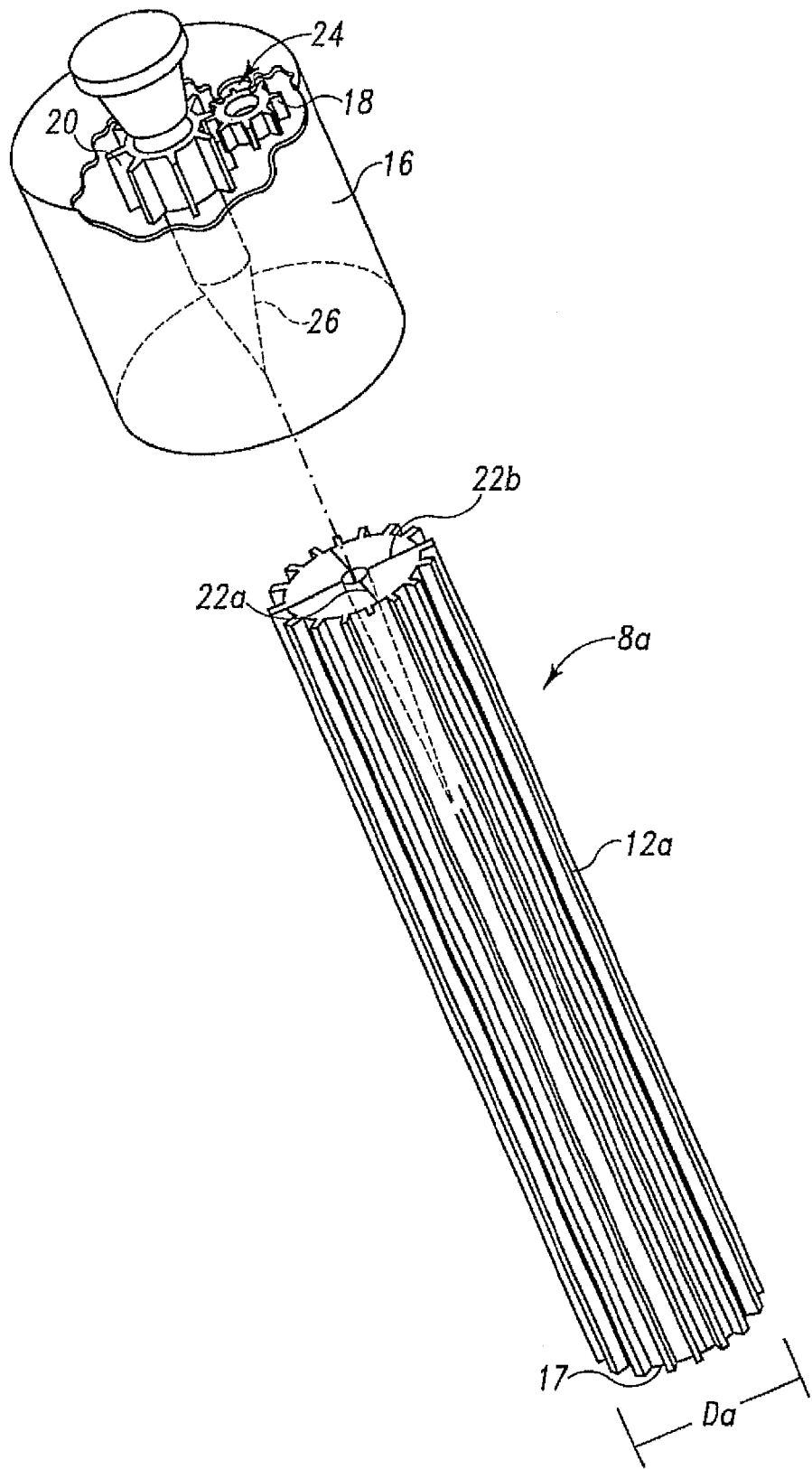
FIG. 2 is a plan view of an expandable distal reamer according to one embodiment of the present invention.

Turning now to FIG. 2, an embodiment of an expandable distal reamer 8a is shown. Because the distal reamer 8a is expandable, the diameter $D_a$ of the distal reamer 8a is variable, unlike the fixed diameters of the prior art distal reamers.

As shown in FIG. 2, the expandable distal reamer 8a includes a proximal portion 16 and a distal cutting portion 17. The proximal portion 16 includes at least two gears 18, 20 that are in contact with each other such that when the gear 18 is rotated, the gear 20 also rotates. Similar to the distal reamer 8 of FIG. 1, the expandable distal reamer 8a includes flutes 12a. The flutes 12a expand outwardly from the reamer 8a when the gears 18, 20 are activated. The reamer 8a also includes a plurality of slits, or cuts, 22a, 22b around its circumference. Such slits 22a, 22b allow the diameter $D_a$ of the expandable distal reamer 8a to enlarge when the gears 18, 20 are rotated.

The gear 18 may be activated by inserting a chuck (not shown) into a hole 24 of the proximal portion 16 and then rotating the chuck. Alternatively, a gauge 25 (FIG. 2a) may be inserted into the hole 24 until it engages the gear 18 and rotated a desired amount. The gauge 25 may include markers 27 (FIG. 2a) to allow the user to know when to stop rotating the gauge. Any other known method for activating a gear may also be utilized.

Once the gears 18, 20 are activated, the gear 20 forces a cone 26 down through the proximal portion 16 into the distal cutting portion 17. As the cone 26 moves downwardly, the cone's increasing diameter forces the distal cutting portion 17 to become enlarged. As stated above, the reamer 8a includes slits 22a, 22b. These slits 22a, 22b allow the distal portion 17 to expand as the cone 26 pushes further into the distal portion 17. Therefore, the diameter Da of the reamer 8a also increases.

Figure 2A:
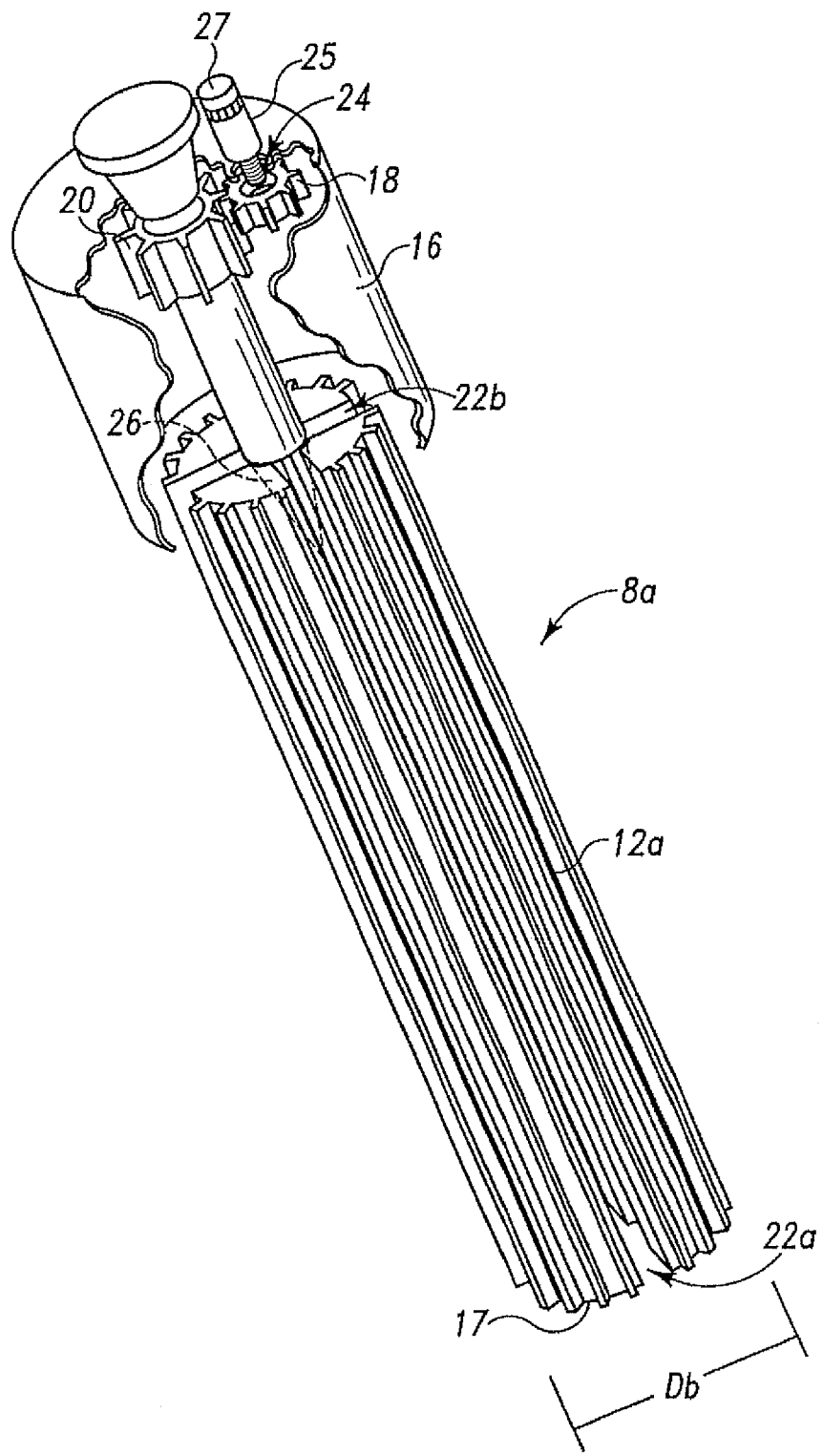
FIG. 2a is a plan view of the expandable distal reamer of FIG. 2 in an expanded position, including a view of the internal components of the reamer.

In FIG. 2a, the gauge 25 is shown inserted into the top of the expandable distal reamer 8a and the distal reamer 8a is shown in an expanded position, having a radius $D_b$. When the gauge 25 is inserted, it engages the gear 18. The gauge 25 may include markings 27 that correlate to the size of the diameter $D_a$ of the expandable distal reamer 8a. In other words, if the surgeon or other healthcare professional rotates the gauge 25 a particular amount, the marking 27 indicates that the rotation correlates to a particular diameter $D_a$ of the expandable distal reamer 8a. Furthermore, as the gauge 25 is rotated, the slits 22a, 22b enlarge as shown in FIG. 2a, creating the larger diameter $D_b$.

As shown in FIGS. 2 and 2a, the diameter $D_a$ of the expandable distal reamer 8a may be enlarged through mechanical means such as gears 18, 20. However, other devices, such as pneumatic or hydraulic mechanisms could also be used to adjust the diameter $D_a$ of the expandable distal reamer 8a. In addition, other mechanical devices, such as cross-bars and/or levers could be used to increase the diameter $D_a$ of the expandable distal reamer 8a.

Figure 3:
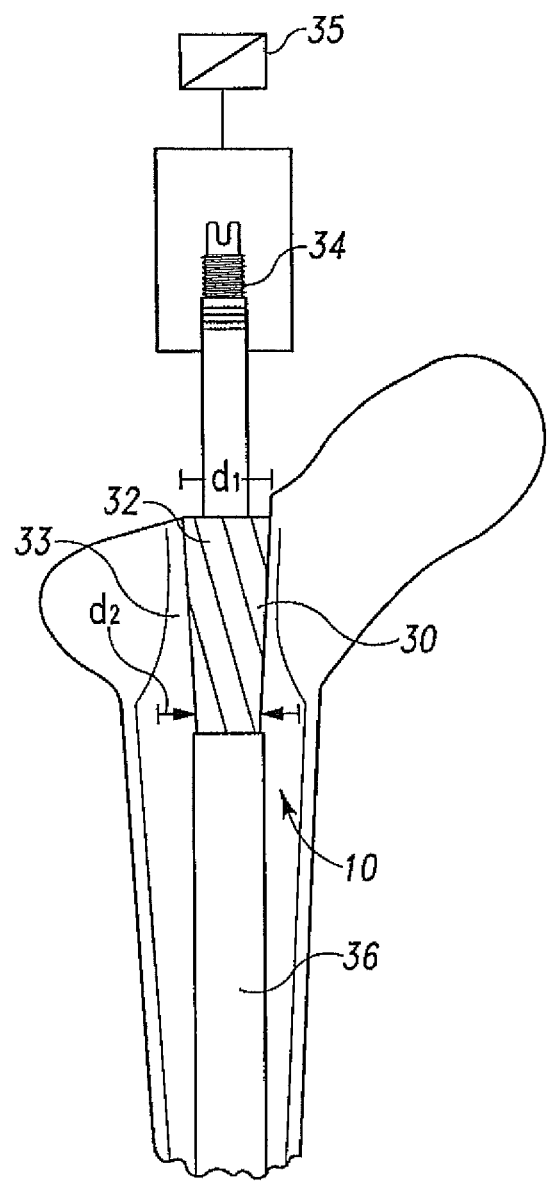
FIG. 3 is a plan view of a proximal reamer in position in a long bone for preparing a bone canal for receiving a long bone prosthetic stem.

After the distal region of the femur 2 is reamed, the proximal portion must then be reamed. As shown in FIG. 3, a conical or proximal reamer 30 is used to form cavity 10 for receiving an orthopedic joint implant. The proximal reamer 30 includes a plurality of longitudinally extending channels or flutes 32 which are used to remove bone and other biological matter from the femur 2 to form a cavity 33 having a cone-shape, with a diameter varying between a diameter $d_1$ to $d_2$, which is the same shape and diameter range of the cone-shaped proximal reamer 30. The proximal reamer 30 may be rotated by use of a connector 34 positioned on the proximal reamer 30. The connector 34 may be any standard connector for example a Hudson or an A-O connector. The connector 34 is used to connect to a power tool 35 for rotating the proximal reamer 30. The power tool 35 may be any standard power tool. It should be appreciated that the proximal reamer 30 may be rotated through the use of the connector 34 by a hand tool for example a "T" shaped handle. The proximal reamer 30 is coupled to a pilot shaft 36 that fits into the reamed cavity 10. The pilot shaft 36 ensures that the proximal reamer 30 goes into the canal and reams straight.

Figure 4:
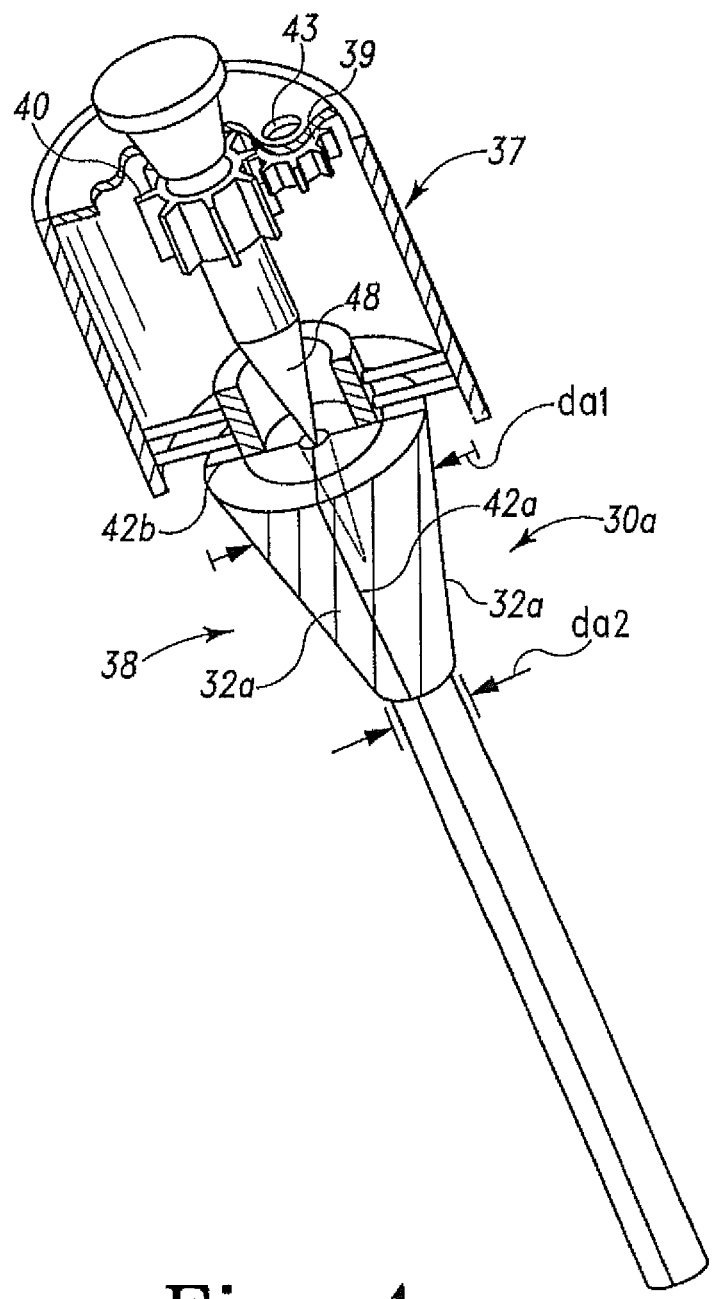
FIG. 4 is a plan view of an expandable proximal reamer according to one embodiment of the present invention.

Turning now to FIG. 4, an expandable proximal reamer 30a according to one embodiment of the present invention is illustrated. Because the proximal reamer 30a is expandable, the diameters $d_{a1}$-$d_{a2}$ of the proximal reamer 30a are variable, unlike the fixed diameters of the prior art proximal reamers.

Similar to the distal reamer 8a shown in FIGS. 2 and 2a above, the proximal reamer includes a proximal portion 37 and a distal cutting portion 38. The proximal portion 37 includes at least two gears 39, 40 that are in contact with each other such that when the gear 39 is rotated, the gear 40 also rotates. Similar to the proximal reamer 30 of FIG. 3, the expandable proximal reamer 30a includes flutes 32a. The flutes 32a expand outwardly from the reamer 30a when the gears 39, 40 are activated. The reamer 30a also includes a plurality of slits, or cuts, 42a, 42b, around its circumference. Such slits 42a, 42b, allow the diameters $d_{a1}$ and $d_{a2}$ of the expandable proximal reamer 30a to enlarge when the gears 39, 40 are rotated.

The gear 39 may be activated by inserting a chuck (not shown) into a hole 43 of the proximal portion 16 and then rotating the chuck. Alternatively, a gauge 44 (FIG. 4a) may be inserted into the hole 43 until it engages the gear 39 and rotated a desired amount. The gauge 44 may include markers 46 (FIG. 4a) to allow the user to know when to stop rotating the gauge. Any other known method for activating a gear may also be utilized.

Once the gears 39, 40 are activated, the gear 40 forces a cone 48 down through the proximal portion 37 into the distal cutting portion 38. As the cone 48 moves downwardly, the cone's increasing diameter forces the distal cutting portion 38 to become enlarged. As stated above, the reamer 30a includes slits 42a, 42b. These slits 42a, 42b allow the distal portion 38 to expand as the cone 48 pushes further into the distal portion 38. Therefore, the diameters $d_{a1}$ and $d_{a2}$ of the proximal reamer 30a also increase.

Figure 4A:
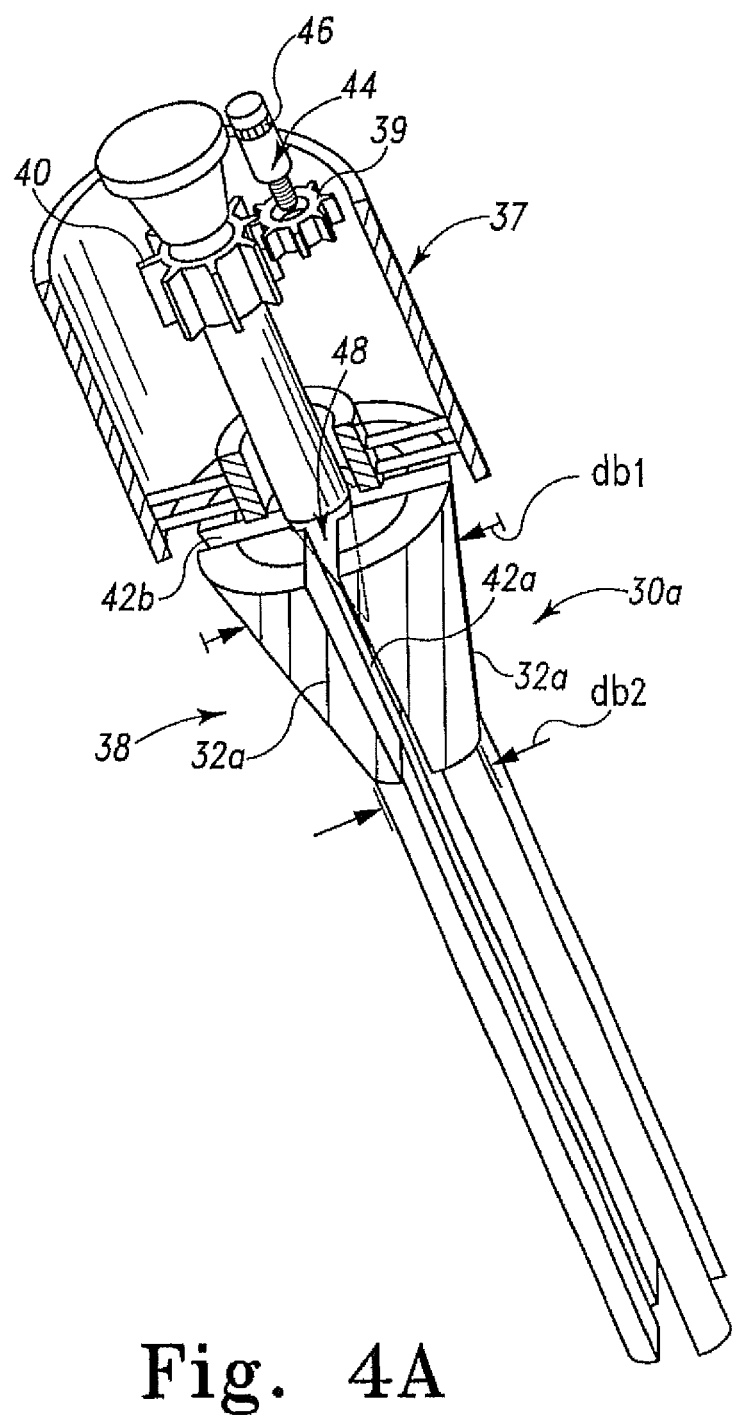
FIG. 4a is a plan view of the expandable proximal reamer of FIG. 4 in an expanded position, including a view of the internal components of the reamer.

In FIG. 4a, the gauge 44 is shown inserted into the top of the expandable proximal reamer 30a and the reamer is shown in an expanded position having diameters $d_{b1}$ and $d_{b2}$ that are greater than the diameters $d_{a1}$ and $d_{a2}$. The gauge 44 may include markings 46 that correlate to the size of the diameters $d_{a1}$ and $d_{a2}$ of the expandable proximal reamer 30a. In other words, if the surgeon or other healthcare professional rotates the gauge 44 a particular amount, the marking 46 indicates that the rotation correlates to particular diameters $d_{a1}$ and $d_{a2}$ of the expandable proximal reamer 30a. Furthermore, as the gauge 44 is rotated, the slits 42a, 42b enlarge as shown in FIG. 4a, creating the larger diameters $d_{b1}$ and $d_{b2}$. In this embodiment, because of the conical shape of the reamer 30a, as the gears 39, 40 are rotated, the diameter $d_{a1}$ increases more relative to the diameter $d_{a2}$. In other words, proximal portion 37 is expanded more relative to the distal portion 38.

As shown in FIGS. 4 and 4a, the diameters $d_{a1}$ and $d_{a2}$ of the expandable proximal reamer 30a may be enlarged through mechanical means such as gears 39, 40. However, other devices, such as pneumatic or hydraulic mechanisms could also be used to adjust the diameters $d_{a1}$ and $d_{a2}$ of the expandable proximal reamer 30a. In addition, other mechanical devices, such as cross-bars and/or levers could be used to increase the diameters $d_{a1}$ and $d_{a2}$ of the expandable proximal reamer 30a.

Figure 5:
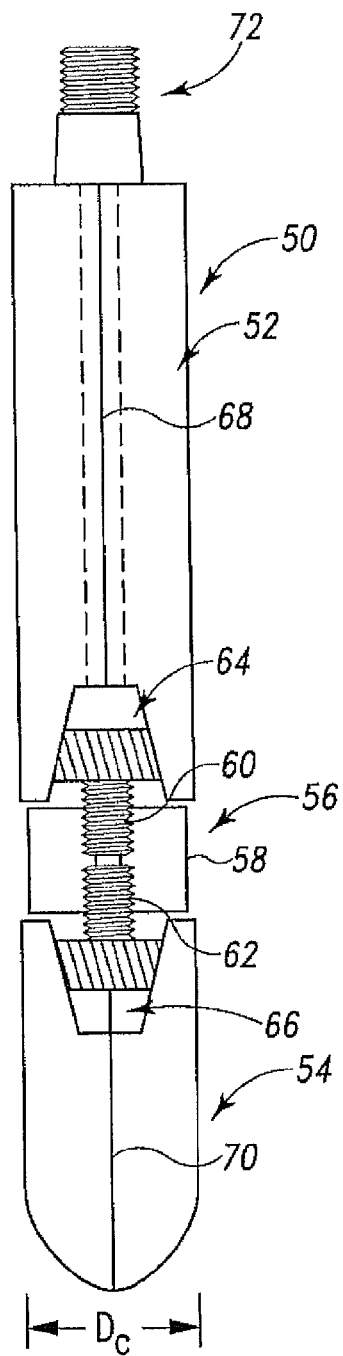
FIG. 5 is a plan view of an expandable pilot shaft according to another embodiment of the present invention.
Figure 5A:
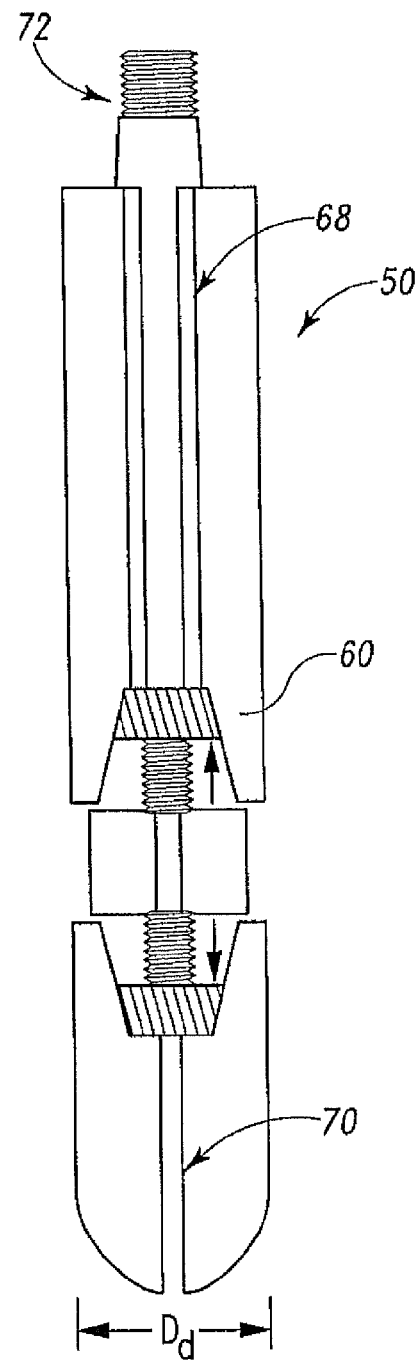
FIG. 5a is a plan view of the expandable pilot shaft of FIG. 5, including a view of the internal components of the shaft.

Turning now to FIGS. 5 and 5a, an alternative embodiment of a pilot shaft 50 is shown. As discussed above, a pilot shaft is attached to the proximal reamer to ensure that the reamer properly extends downwardly into the canal. Also as discussed above, because the distal reamer 8 may come in various sizes, the pilot shaft must also come in a variety of sizes. Therefore, to cut-down on manufacturing costs and to reduce the possibility of confusion in the operating room, in one embodiment of the present invention, the pilot shaft 50 is also adjustable. As shown in FIG. 5, the pilot shaft 50 includes a proximal portion 52, a distal portion 54 and a central portion 56. The central portion 56 includes a sleeve 58 that engages two threaded screws 60, 62. As the sleeve 58 is rotated, the threaded screws 60, 62 are pushed into openings 64, 66 in the proximal and distal portions 52, 54. The proximal and distal portions 52, 54 each include slits 68, 70 that open as the threaded screws 60, 62 are pushed into the openings 64, 66 (as shown in FIG. 5a). Thus, the operator is able to adjust the diameter of the pilot shaft 50 to match the diameter of the reamed canal 10. In the embodiments illustrated in FIGS. 5 and 5a, the pilot shaft 50 is adjusted from having a diameter of $D_c$ to $D_d$. As shown in FIGS. 5 and 5a, the pilot shaft 50 also includes a connectable mechanism such as a threaded portion 72 for attachment to the expandable proximal reamer 30a. Alternatively, the threaded portion 72 may also attach to a miller shell or a proximal body trial (not shown).

Figure 6:
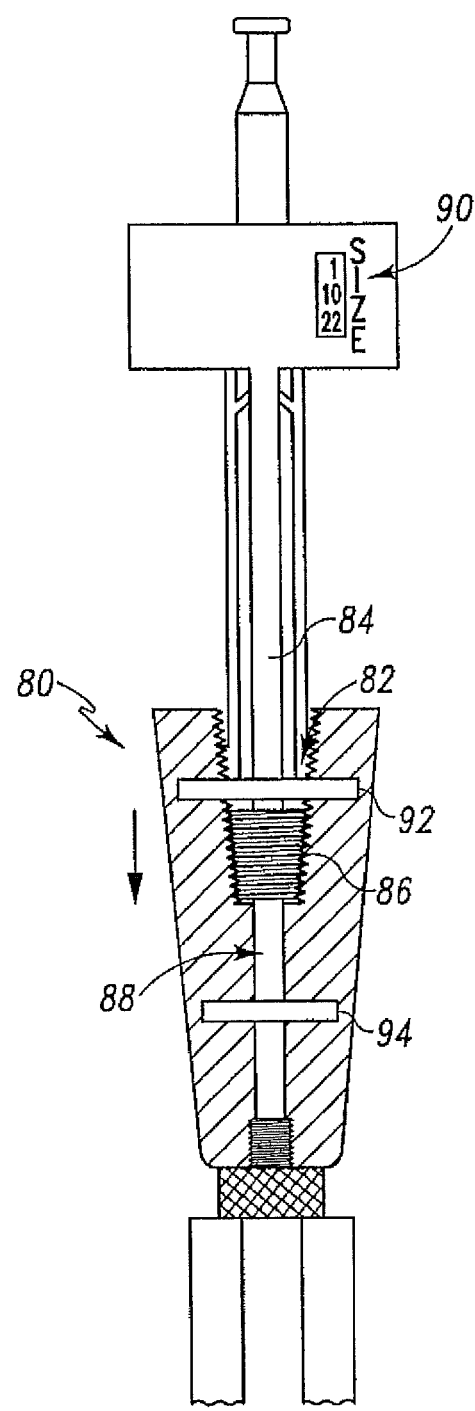
FIG. 6 is a plan view of an expandable proximal reamer according to another embodiment of the present invention.

Turning now to FIG. 6, an alternative embodiment of an expandable proximal reamer 80 is illustrated. In this embodiment, the expandable proximal reamer 80 includes an upper conical recess 82. A threaded expansion rod 84 has a threaded end 86 and is inserted into the upper conical recess 82. As the threaded expansion rod 84 is advanced through the upper conical recess 82, the expandable reamer 80 is widened through the use of a slit 88. The user may thus adjust the diameters of the expandable reamer 80.

As shown in FIG. 6, the threaded expansion rod 84 may include a gauge 90, allowing the user to determine the diameter of the reamer 80. Also, the rod 84 may include upper and lower support rods 92, 94 that extend into the reamer 80 to keep the reamer 80 and the rod 84 rigid during use. Either or both of the support rods may also be used in connection with any of the embodiments discussed above.

In all of the embodiments discussed above, whether for distal reamers, proximal reamers, or pilot shafts, the various gauges and/or markings may also include preset stops that correspond to certain sizes. Such preset stops would make it easier for a user to accurately stop adjusting at the correct diameter. The preset stops may be fashioned out of notches in a thread or any other known mechanism.

Figure 7:
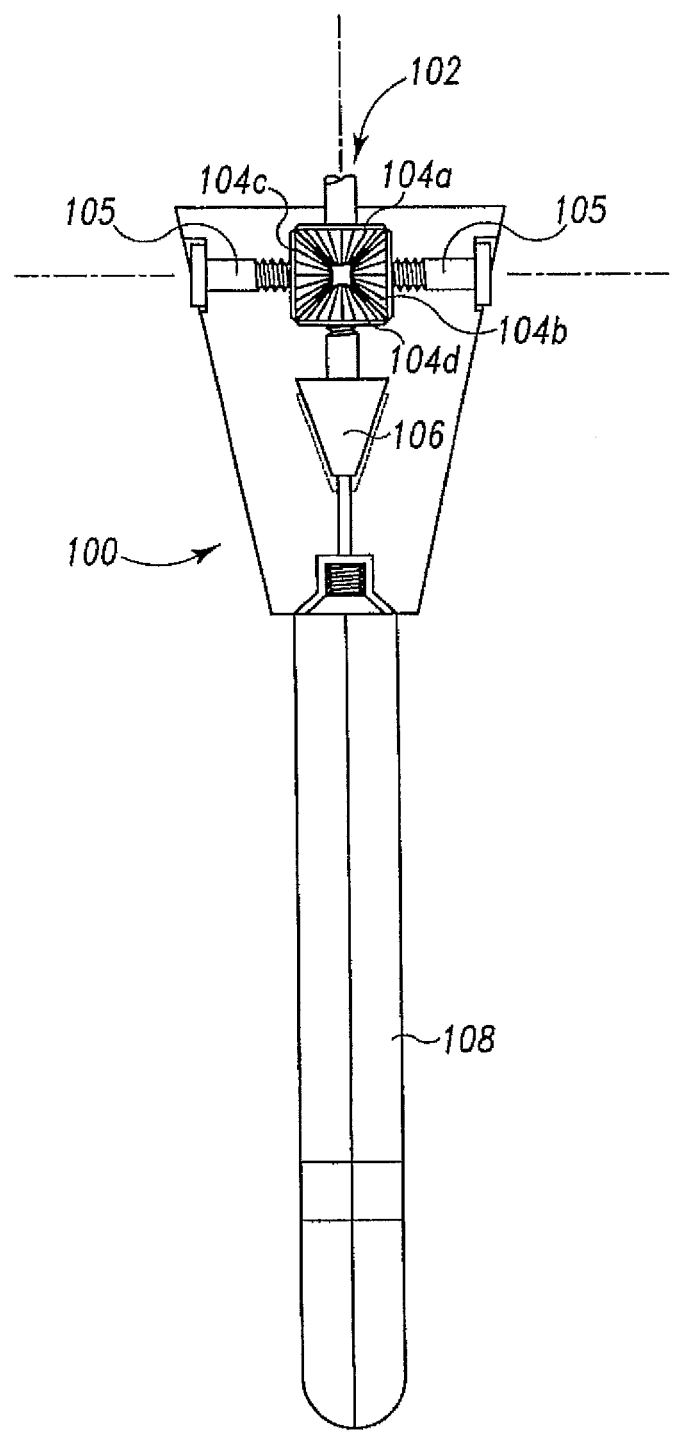
FIG. 7 is a plan view of an expandable proximal reamer according to yet another embodiment of the present invention.

Turning now to FIG. 7, another embodiment of an expandable proximal reamer 100 is illustrated. In this embodiment, the proximal reamer 100 includes a screw 102 that extends outwardly from the proximal reamer 100. The screw 102 has a threaded portion 104a that is threadably engaged with threaded portions 104b, 104c of supports 105. The supports 105 provide the reamer 100 with support during cutting, enabling the reamer 100 to expand, yet still maintain its strength and rigidity.

As a user rotates the screw 102, the threads 104a cause the threaded portions 140b, 104c to also rotate. The threaded portions 104b, 104c are also threadably engaged with a thread 104d, such that when the threaded portions 104b, 104c are rotated, the threaded portion 104d also rotates. The threaded portion 104d is coupled to a cone 106, such that as the threaded portion 104d rotates, the cone 106 moves in a downward direction 112 (FIG. 7a), causing the proximal reamer 100 to expand outwardly in the direction indicated by arrows 114. This also causes the supports 105 to move outwardly in directions 110 as shown in FIG. 7a.

Figure 7A:
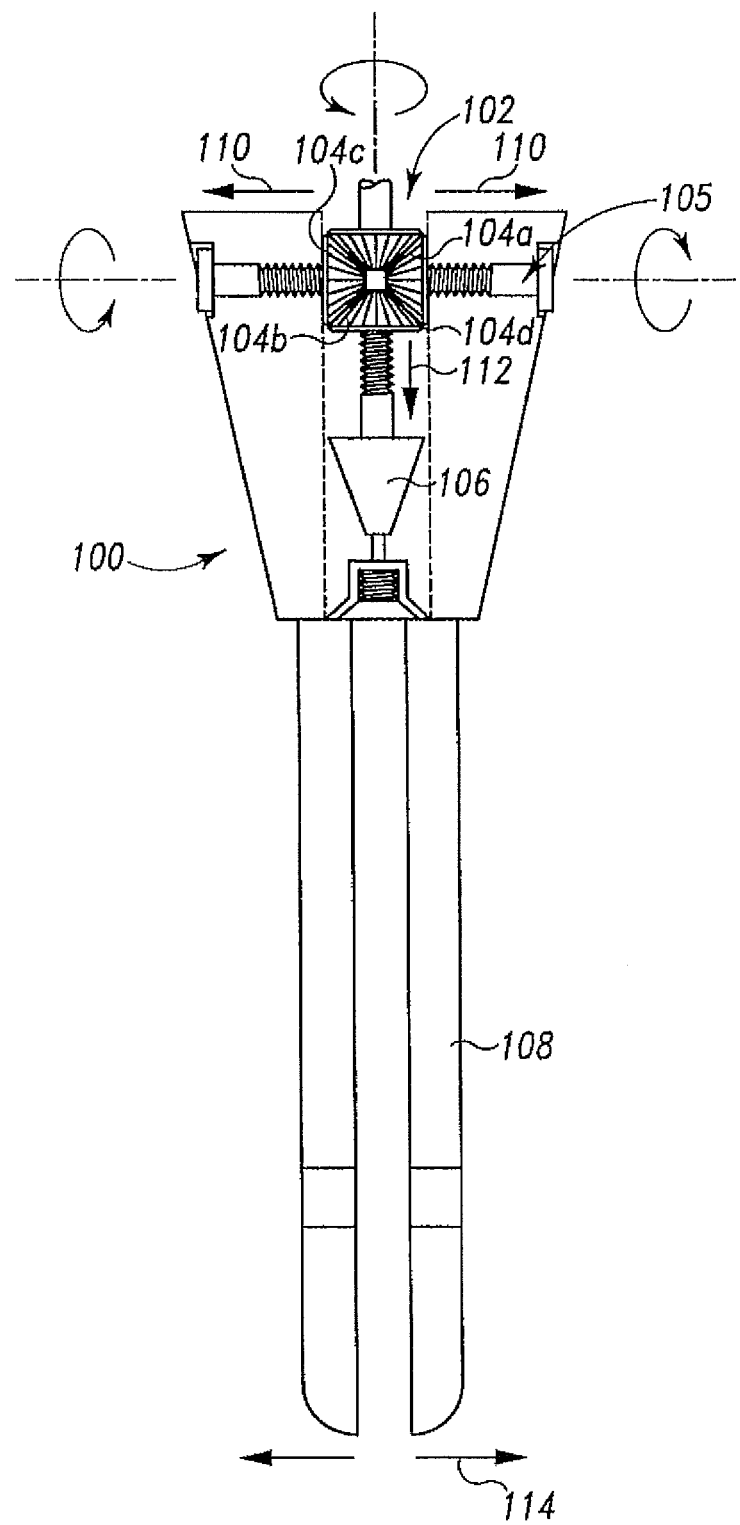
FIG. 7a is a plan view of the expandable proximal reamer of FIG. 7 in an expanded state.

As shown in FIGS. 7 and 7a, the proximal reamer 100 is coupled to a pilot shaft 108, such that as the cone 106 moves downwardly, the pilot shaft 108 may also expand in an outward direction as indicated by arrows 114 (FIG. 7a).

Figure 8:
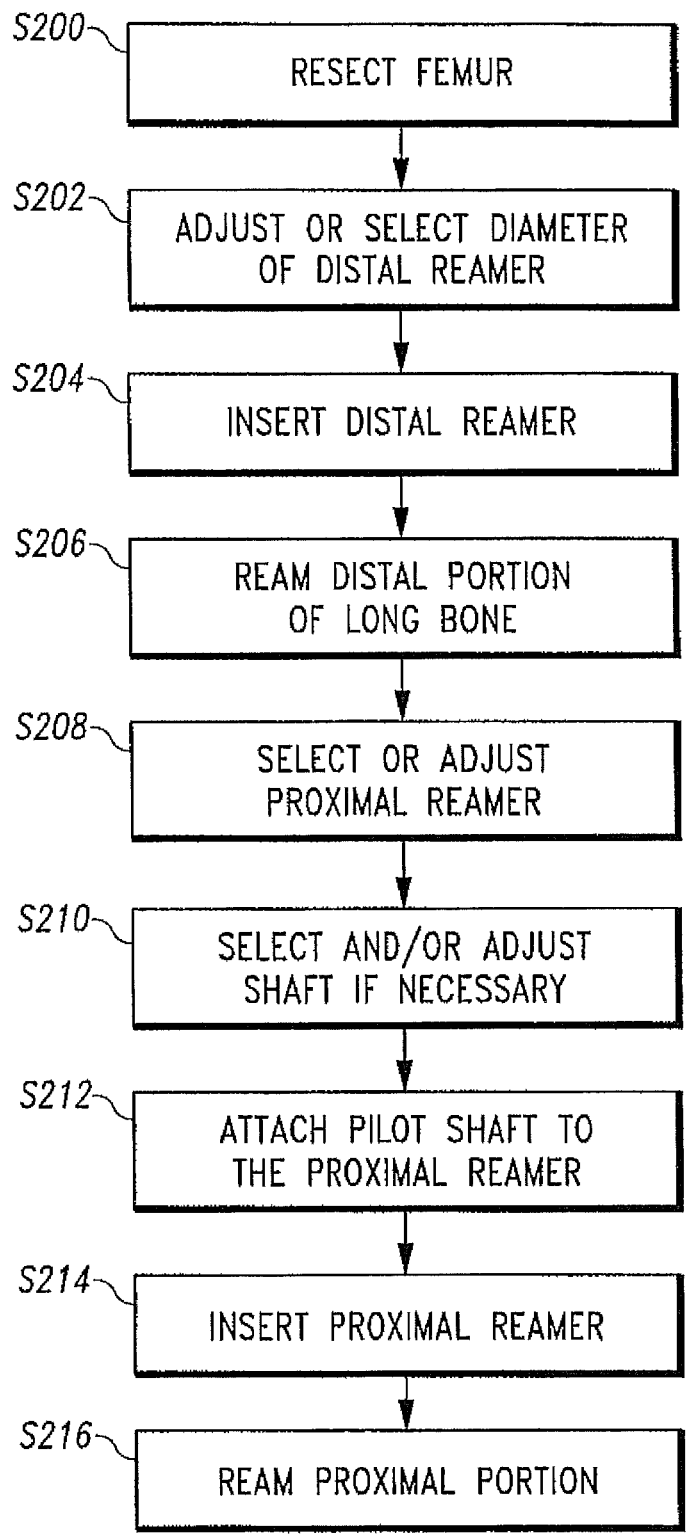
FIG. 8 is a flow chart illustrating a method of using an expandable reamer according to one embodiment of the present invention.

Turning now to FIG. 8, a method for utilizing the expandable reamers is shown. At step s200, the femur is resected. Next, the user selects the distal reamer to be used at step s202. If an expandable distal reamer is to be used, then at step s202, the user then adjusts the diameter of the distal reamer as described above. At step s204, the distal reamer is inserted and the distal portion of the long bone is reamed (step s206). Next, at step s208, the proximal reamer is selected. If the proximal reamer is an adjustable reamer, the user will adjust the proximal reamer to the appropriate diameter. If the proximal reamer is not adjustable, then the user must select a proximal reamer with an appropriate diameter from a set of reamers. Next, at step s210, the pilot shaft is selected or adjusted as necessary. At step s212, the proximal reamer is attached to a pilot shaft. The proximal reamer and shaft are inserted into the proximal portion of the long bone and the reamed distal portion, respectively at step s214. The proximal portion is then reamed at step s216. The rest of the reaming and implantation process is then completed in any of the ways customary and known in the prior art. It should be noted that although in this example, both the proximal reamer and the distal reamer were expandable, that in some embodiments, only one of the reamers may be expandable. Also, while some embodiments refer to an adjustable pilot shaft, in other embodiments, the pilot shafts of the prior art may be attached to the proximal reamers.

Figure 9:
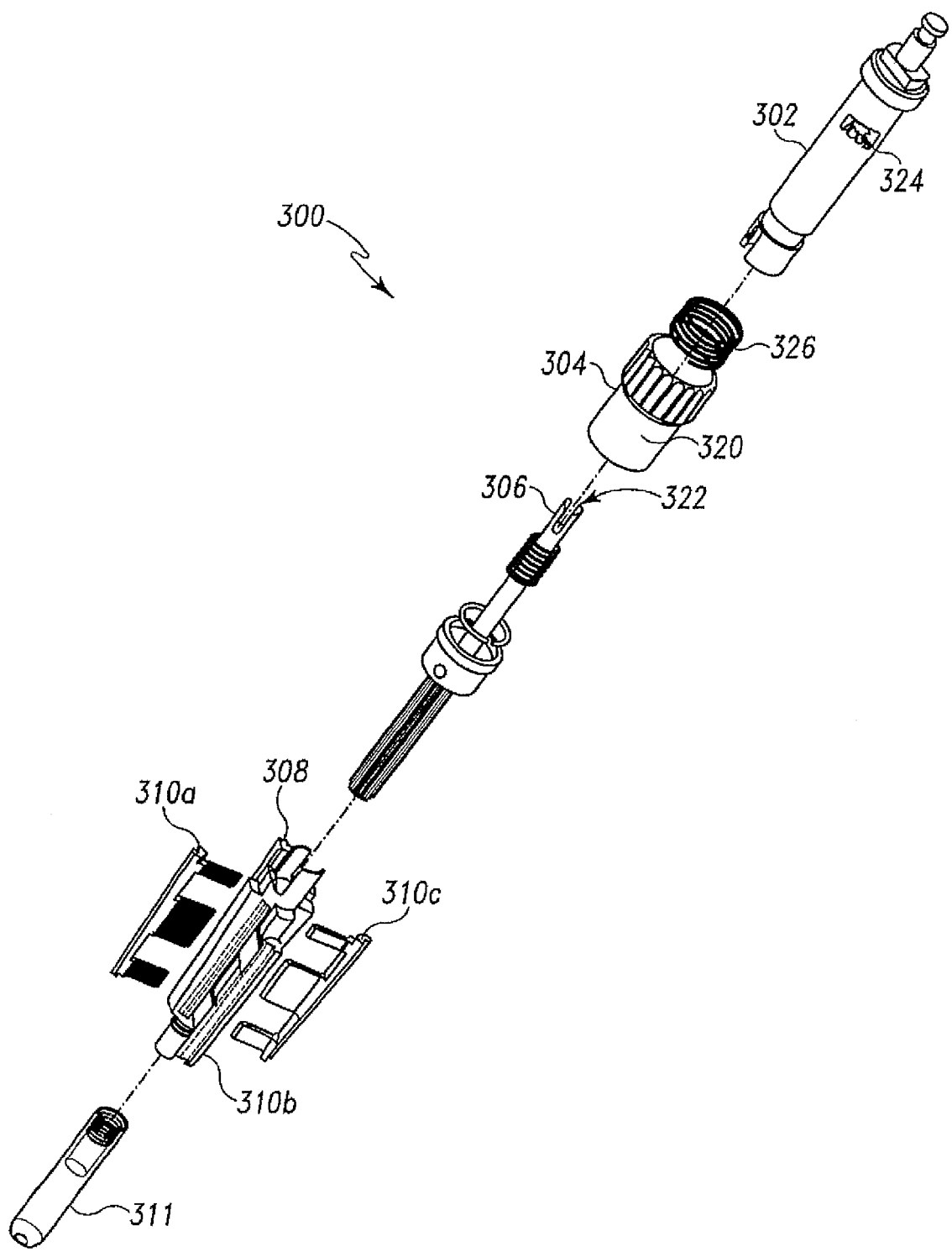
FIG. 9 is an exploded view of the expandable reamer according to another embodiment of the present invention.

Turning now to FIG. 9, an exploded view of another embodiment of an expandable reamer 300 is shown. The expandable reamer 300 includes a handle 302, knob 304, actuator rod 306, body 308, a plurality of cutting edges 310a, 310b, 310c, 310d and a pilot shaft 311.

Figure 10:
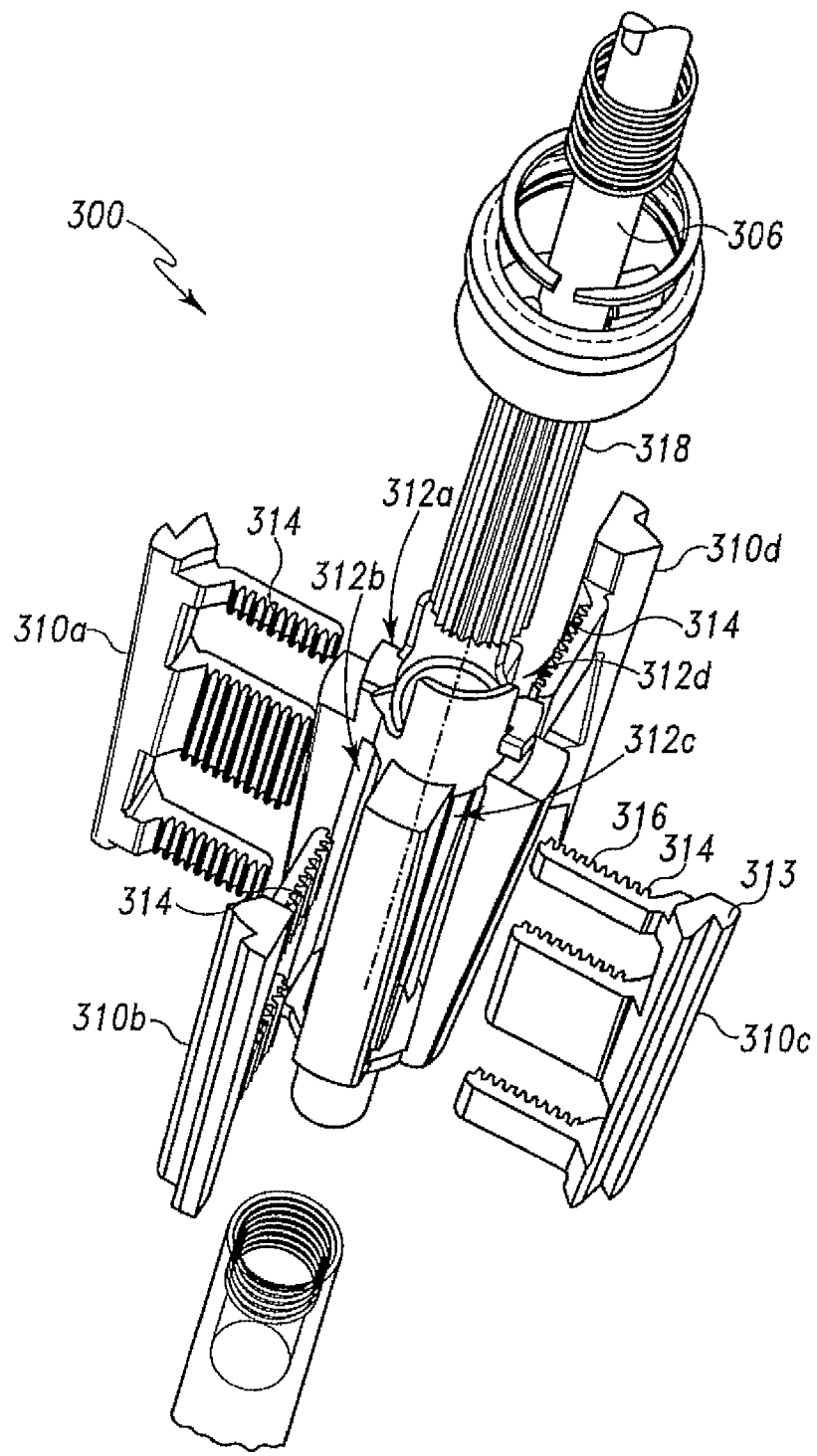
FIG. 10 is a close-up view of the body and cutting edges of the expandable reamer of FIG. 9.

Turning now to FIG. 10, the relationship between the body 308 and the cutting edges 310 will be described. The body 308 includes a plurality of slots 312a, 312b, 312c, 312d. As shown, the plurality of cutting edges 310a, 310b, 310c, 310d extend through the slots 312a, 312b, 312c, 312d. Each of the cutting edges 310a, 310b, 310c, 310d include a cutting edge side 313 and an opposite side 314. The opposite side includes a plurality of gear teeth 316.

The plurality of gear teeth 316 engages a gear 318 on the actuator rod 306. The gear teeth 316 and the gear 318 are engaged such that when an operator turns the rod 306, the gear 318 causes the gear teeth 316 to move, thereby expanding a diameter of the reamer 300. The diameter expansion will be explained in more detail in reference to FIGS. 11a and 11b below.

Turning back to FIG. 9, the knob 304 includes a pin 320 that engages a slot 322 in the actuator rod 306. The pin 320 also engages a notched slot 324 in the handle 302. The notched slot 324 allows the user to lock the pin 320 at certain locations, thereby locking the actuator rod 306 (and, as a result the cutting edges 310a, 310b, 310c, 310d) in a particular location. There is also included a spring 326 that aids in holding the pin 320 in one of the notches of the notched slot 324. To release the pin 320, the user would pull up and turn the handle 302 to disengage the pin 320 from the particular notch in the notched slot 324 with or without the assistance of other gears and gear ratios. In other words, in some embodiments, there may be additional gears that engage the gear 318. The additional gears allow the surgeon or other user to move the actuator rod 306 more than the gear 318 moves.

Figure 11A:
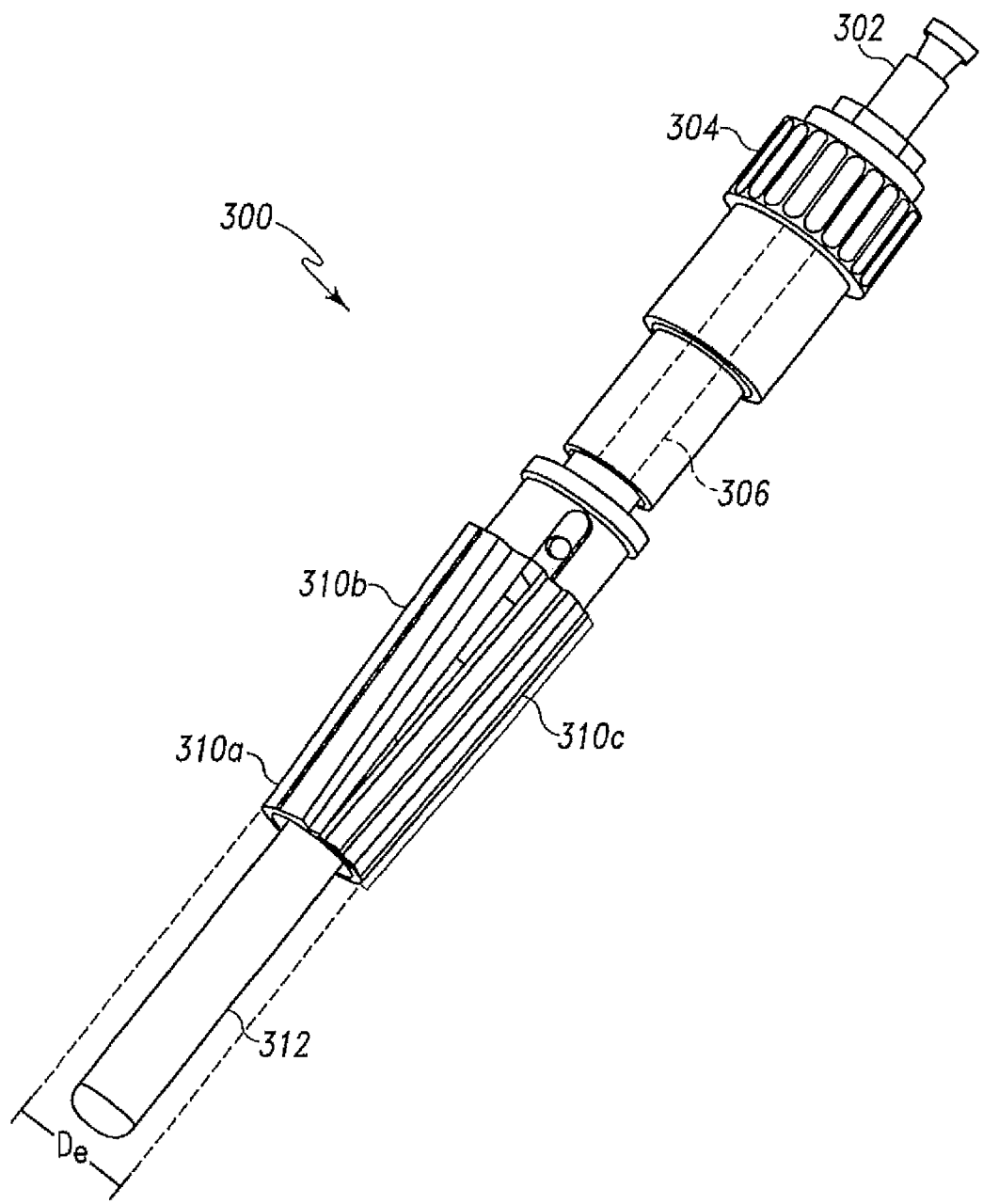
FIG. 11a is a plan view of an expandable reamer of FIG. 9.
Figure 11B:
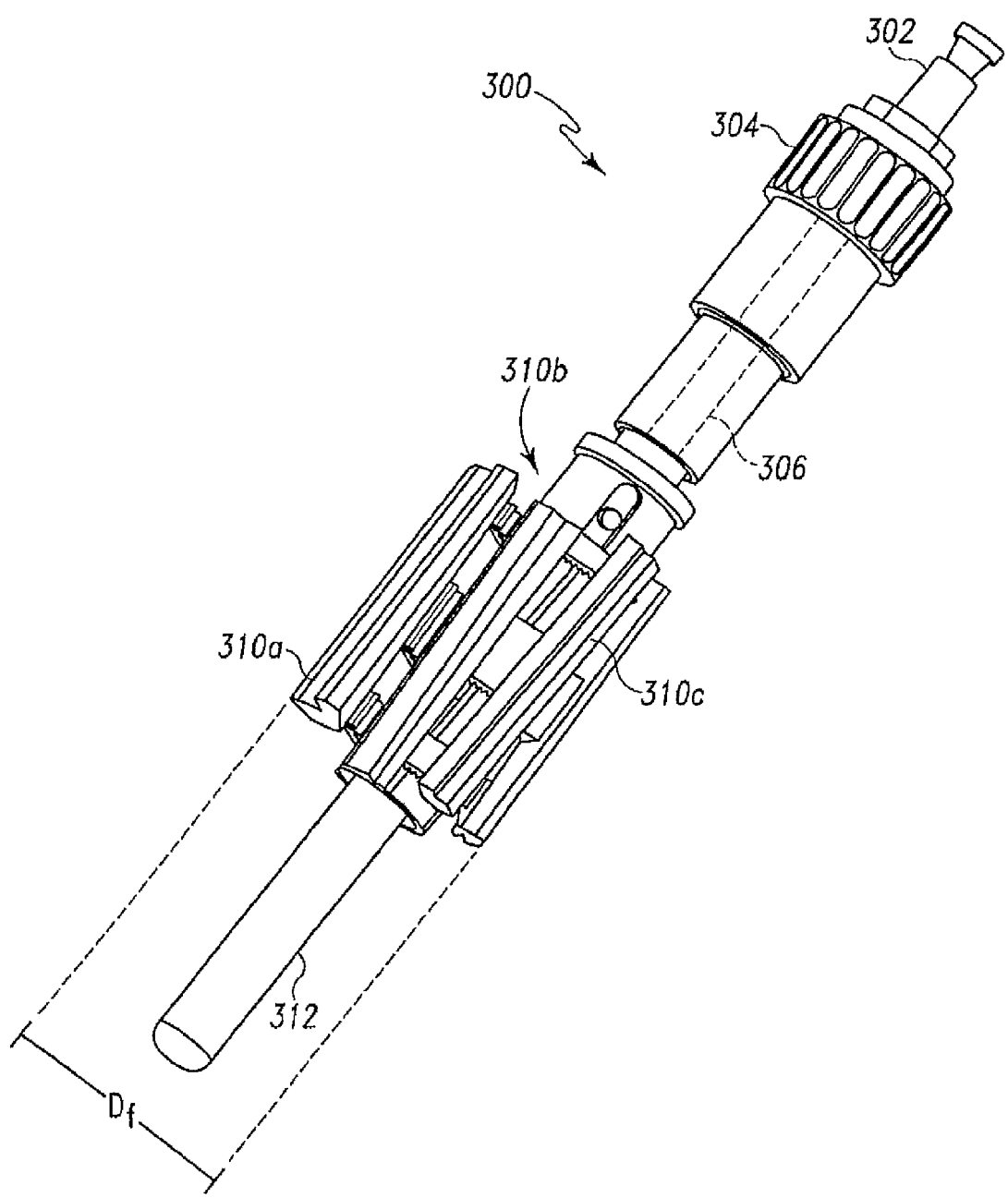
FIG. 11b is a plan view of the expandable reamer of FIG. 9 in an expanded state.

Turning now to FIGS. 11a and 11b, the reamer 300 will be shown in non-expanded and expanded views. In the non-expanded view shown in FIG. 11a, the cutting edges 310a, 310b, 310c, 310d creating a cutting diameter $D_e$. As shown in FIG. 11b, once the knob 304 is turned, the cutting edges 310a, 310b, 310c, 310d create an expanded cutting diameter $D_f$ that is larger than the cutting diameter $D_e$.

The embodiment illustrated in FIGS. 9-11b is a proximal reamer that is generally cone-shaped. However, the reamer 300 may also be a distal reamer, and be generally cylindrical-shaped. In other embodiments, the cutting edges 310a, 310b, 310c, 310d may be replaced with non-cutting edges and the device may be used as an expandable instrument. In other words, the concept of the body 308, edges 310a, 310b, 310c, 310d, and actuator rod 306 may be used in any type of instrument where it is desirable to have an expandable diameter. Although four cutting edges 310a, 310b, 310c, 310d have been illustrated, any number of cutting edges may be used.

In some embodiments of the present invention, the reamer may be a combination of the reamer 300 of FIGS. 9-11b and the reamer 30a of FIG. 4. In this alternative embodiment, the reamer utilizes the gear 318 and cutting edges 310a, 310b, 310c, 310d of FIG. 9 as well as the cone 48 from FIG. 4. As described in reference to FIG. 4, the increasing diameter of the cone 48 forces the cutting edges 310a, 310b, 310c, 310d to expand. Although four cutting edges have been described any number of cutting edges may be use.

In some embodiments of the present invention, a kit for reaming the long bone is provided, including distal reamers, proximal reamers, and pilot shafts. The kit includes at least one reamer that is an expandable reamer. In some embodiments, both the distal reamer and the proximal reamers will be expandable. In other embodiments, only one of the types of reamer will be expandable. In some embodiments, the pilot shaft may also be expandable.

According to some embodiments of the present invention, the expandable reamers may be able to expand to all sizes required for that type of reamer. In other embodiments, the expandable reamers may only expand through a range, and a plurality of reamers may still be required. For example, if the expandable reamer is a proximal reamer, a kit may include three expandable proximal reamers. Each expandable proximal reamer in such a kit has a diameter that is variable within a range.

Although the present invention and its advantages have been described in detail, it should be understood that various changes, substitutions, and alterations can be made therein without departing from the spirit and scope of the present invention as defined by the appended claims.

The invention claimed is:

1. A method for reaming a portion of a long bone cavity with a reamer for use in implanting a joint prosthesis, the reamer for cooperation with a portion of an orthopaedic implant component, the method comprising; reaming a cylindrical portion of the long bone using a cylindrical reamer; and reaming a conical portion of the long bone using a conical reamer; wherein at least one of the cylindrical reamer and conical reamer is an expandable reamer, such that the at least one of the cylindrical reamer and conical reamer includes a body having a plurality of slots, a plurality of cutting edges extending through the slots, and an actuator rod including a gear for engaging the plurality of cutting edges such that when the actuator rod is turned in one direction, the plurality of cutting edges expands outwardly through the slots, wherein the gear of the actuator rod is a long gear that extends length of each of the plurality of cutting edges and engages a plurality of ridges on the plurality of cutting edges, wherein the plurality of cutting edges include a cutting side and a ridge side such that the ridge side includes the ridges.

2. The method of claim 1, wherein the conical reamer includes a distal region and a proximal region and the diameter of the conical region is expanded more relative to the distal region.

3. The method of claim 1, wherein the conical reamer is a proximal reamer and the cylindrical reamer is a distal reamer.

4. The method of claim 1, wherein the gear of the actuator rod engages the cutting edges such that when the actuator rod is turned in an opposite direction the cutting edges retract into the slots.

* * * * *